US011813187B2

(12) United States Patent
Sacco

(10) Patent No.: US 11,813,187 B2
(45) Date of Patent: Nov. 14, 2023

(54) WEARABLE DEVICE TO REDUCE PAIN AND PROMOTE HEALING OF LOWER BACK PROBLEMS

(71) Applicant: Paul Sacco, Greeley, CO (US)

(72) Inventor: Paul Sacco, Greeley, CO (US)

( * ) Notice: Subject to any disclaimer, the term of this patent is extended or adjusted under 35 U.S.C. 154(b) by 67 days.

(21) Appl. No.: 16/938,391

(22) Filed: Jul. 24, 2020

(65) Prior Publication Data

US 2021/0069000 A1    Mar. 11, 2021

Related U.S. Application Data

(63) Continuation of application No. 15/788,191, filed on Oct. 19, 2017, now abandoned.

(51) Int. Cl.
| | |
|---|---|
| *A61F 5/00* | (2006.01) |
| *A61F 5/02* | (2006.01) |
| *A61F 5/042* | (2006.01) |
| A61F 5/04 | (2006.01) |

(52) U.S. Cl.
CPC ............ *A61F 5/028* (2013.01); *A61F 5/02* (2013.01); *A61F 5/024* (2013.01); *A61F 5/042* (2013.01); *A61F 5/04* (2013.01)

(58) Field of Classification Search
CPC .. A61F 5/02; A61F 5/022; A61F 5/024; A61F 5/026; A61F 5/028; A61F 5/03; A61F 5/0553; A61F 5/042; A61F 5/048; A61H 1/0292; A61H 1/0229; A61H 3/02
USPC ...... 128/96.1, 100.1; 602/18, 17, 16, 12, 32, 602/36
See application file for complete search history.

(56) References Cited

U.S. PATENT DOCUMENTS

| | | | |
|---|---|---|---|
| 2,886,031 A | * | 5/1959 | Robbins ................. A61F 5/024 602/19 |
| 3,029,810 A | * | 4/1962 | Martin .................... A61F 5/024 248/407 |
| 3,351,053 A | | 11/1967 | Stuttle |
| 3,420,230 A | | 1/1969 | Ballard |
| 3,434,469 A | | 3/1969 | Swift |
| 3,521,623 A | | 7/1970 | Nichols et al. |
| 4,708,130 A | | 4/1987 | Grudem |
| D291,005 S | | 7/1987 | Berlese |
| 4,691,696 A | | 9/1987 | Farfan de los Godos |
| 4,715,362 A | | 12/1987 | Scott ....................... A61F 5/024 602/19 |

(Continued)

OTHER PUBLICATIONS

Assorted back devices from Internet searched Aug. 4, 2017.

*Primary Examiner* — Adam Baker
(74) *Attorney, Agent, or Firm* — Clifford H. Kraft

(57) ABSTRACT

A device that decompresses the lower spine while the wearer is seated or standing. The device includes two belt-shaped straps. The first strap circles the upper torso just below the breast line. The second strap circles the waist at or slightly above the normal belt line riding on the hip. In embodiments of the invention, the lower strap can be a normal belt. The straps can be equipped with pockets that are aligned along the upper edge of the upper strap and the lower edge of the lower strap designed to receive and hold flat splints. Typically, two rigid flat splints extend vertically between the straps centered laterally on the left and right sides of the torso. When the device is worn, it decompresses the lower spine when the person stands or sits.

18 Claims, 7 Drawing Sheets

(56) References Cited

U.S. PATENT DOCUMENTS

| | | | | |
|---|---|---|---|---|
| 4,721,102 A | * | 1/1988 | Pethybridge | A61F 5/024 602/19 |
| 4,771,768 A | * | 9/1988 | Crispin | A61F 5/0127 D24/190 |
| 4,833,730 A | | 5/1989 | Nelson | |
| 4,907,575 A | * | 3/1990 | Satterthwaite | A61F 5/024 602/19 |
| 5,179,942 A | | 1/1993 | Drullas et al. | |
| 5,445,601 A | | 8/1995 | Harlow | |
| 5,557,801 A | | 9/1996 | Jakus | A41D 13/0051 2/465 |
| 5,776,088 A | * | 7/1998 | Sereboff | A61F 5/34 602/18 |
| 6,099,490 A | | 8/2000 | Turtzo | |
| 6,146,345 A | * | 11/2000 | Mignard | A61F 5/028 602/19 |
| 6,280,405 B1 | | 8/2001 | Broselid | A61F 5/024 128/874 |
| 6,336,908 B1 | | 1/2002 | Slautterback | |
| 6,533,740 B2 | * | 3/2003 | Reinecke | A61F 5/024 602/5 |
| 6,821,261 B2 | | 11/2004 | Doty | A61F 5/0123 128/882 |
| 6,852,088 B2 | | 2/2005 | Gaylord | |
| 7,001,348 B2 | | 2/2006 | Garth et al. | |
| 7,128,724 B2 | | 10/2006 | Marsh | |
| D635,682 S | | 4/2011 | Chiang | |
| D725,786 S | | 3/2015 | Romo et al. | |
| 9,414,955 B2 | | 8/2016 | Safko et al. | |
| D794,809 S | | 8/2017 | Gramza et al. | |
| 2005/0228325 A1 | * | 10/2005 | Zours | A61F 5/024 602/19 |
| 2008/0249448 A1 | * | 10/2008 | Stevenson | A61F 5/0125 602/5 |
| 2014/0276308 A1 | * | 9/2014 | DiAngelo | A61F 5/03 602/19 |
| 2015/0094633 A1 | | 4/2015 | Garcia | A61F 5/026 602/19 |

\* cited by examiner

WEARABLE DEVICE TO REDUCE PAIN AND PROMOTE HEALING OF LOWER BACK PROBLEMS

This is a continuation of application Ser. No. 15/788,191 filed Oct. 19, 2017. Application Ser. No. 15/788,191 is hereby incorporated by reference in its entirety.

BACKGROUND

Field of the Invention

The present invention relates to devices for back problems and more particularly to a wearable device that dramatically reduces pain and promotes healing of Spinal Stenosis, Degenerative Disc Disease, Herniated Discs, Muscle Spasms, and Sciatica.

Description of the Problem Solved and of the Prior Art

Low back pain is the single leading cause of disability worldwide. According to the Global Burden of Disease 2010, an average of 30 million adults experience lower back pain at some point in their lifetimes, and it is the most common cause of job-related disability. Spinal Degenerative Joint Disease describes a number of lower back conditions that primarily affect people when they become older. Spondylosis is a term that refers to the general degeneration of the spine associated with normal wear and tear that occurs in the joints, discs, and bones of the spine as people get older. One of the many mechanical causes of low back pain is a condition called Spinal Stenosis where the spinal canal begins to narrow causing the open spaces between the vertebrae decrease in size. The tightness can pinch the spinal cord and/or or Sciatic Nerve causing pain, tingling, or numbness in the legs, arms, or torso. Common treatments include medications and physical therapy. If the pain cannot be controlled this way, surgery may be recommended. Unfortunately, surgery does not always work. Some spine decompression techniques include ice and even hanging a patient upside-down to relieve the pressure. While hanging upside-down is effective, it is hardly practical as a long-term cure and can even cause strokes if the body remains at more than a 30-degree angle too long.

It has been shown that if the lower back can be decompressed for long periods of time, not only is pain relieved, but also actual healing can take place. Healing cannot occur when the spine is in a compressed state. While extreme techniques like hanging upside down, or engaging in expensive decompression sessions on a specialized mechanical bed at the doctor's office, can result in the desired decompression, these alternatives are simply not practical and can even be dangerous.

U.S. Pat. No. 4,708,130 by Grudem shows an immobilization device that is typically used after back surgery. This device has two splints that are forward of the side of the user's body and a solid back brace member that resides in the center of the back. This device immobilizes the back, but fails to provide decompression while sitting. The forward position of the splints also gets in the way of normal movements and can actually cause pain in the chest when the user tries to bend forward.

U.S. Pat. No. 3,420,230 by Ballard teaches a device with two straps and a single back splint. This device fails to provide decompression when seated or bending forward.

It would be particularly advantageous to have a device that decompressed the lower spine while the user is simply sitting, since sitting is the most comfortable position and is a position that many people must assume at work or leisure for long hours anyway.

SUMMARY OF THE INVENTION

The present invention relates to a device that decompresses the lower spine while the wearer is seated. The device includes two (and in some cases, only one) belt-shaped straps. The first strap circles the upper torso just below the breast line. It can thus be used by women as well as men without putting undue pressure on the breasts. The second strap circles the waist at the normal belt line and rides on the hips. In some embodiments of the invention only one strap is used with the lower strap being a normal belt. The straps are typically equipped with a series of pockets that are aligned along the upper edge of the upper strap and the lower edge of the lower strap that are designed to receive and hold flat splints. In alternate embodiments, the splints can be permanently attached with no pockets. Typically, two rigid flat splints extend vertically between the upper and lower straps on the left and right sides of the torso. With the straps and splints correctly positioned, the device decompresses the lower spine when the user sits and slightly leans forward, or leans from side to side. It maintains maximum decompression as long as the person remains seated. The device, normally worn under the clothes, does not interfere with clothing, movement, work or appearance. Since many people remain seated for long periods each day, the present invention maintains a state of spinal decompression during these long periods. Decompression, in addition to relieving pain, improves posture and allows blood, hydration and nutrients to flow into the problem area and enhance the body's natural healing response. This simply cannot happen when the area is being continually pinched by the natural forces of gravity, much less by other mechanical physical conditions of the spine.

The present invention grips the upper back and hips and performs an expansive motion when the wearer gently leans forward or side to side, expanding the lower spine by simply sitting in a chair. It also creates a gentle expansion while the wearer is standing and engaging in daily activities and sports. It is worn against the skin for best grip and can be comfortably worn on a daily basis for hours during the day under clothing while sitting at a desk or keyboard, or while standing and moving. As a side effect, the present invention helps correct the wearer's posture by making the user sit up straight while simultaneously decompressing the lower spine helping to alleviate pain.

DESCRIPTION OF THE FIGURES

Attention is now directed to several drawings the illustrate features of the present invention.

Several figures and illustrations have been provided to aid in understanding the present invention. The scope of the present invention is not limited to what is shown in the figures.

DESCRIPTION OF THE PREFERRED EMBODIMENTS

The present invention relates to a device that can be worn under clothing to decompress the lower spine relieving pain and promoting healing of lower back problems such as Spinal Stenosis, Degenerative Disc Disease, Herniated Discs, Muscle Spasms, and Sciatica. The device includes an upper strap or belt worn below the breast line and a lower strap or belt worn in the normal belt position riding on the hip. At least two rigid splints extend vertically between the two belts on the left and right sides of the body. When the wearer stands or sits, the lower spine is gently decompressed.

Figure 1:
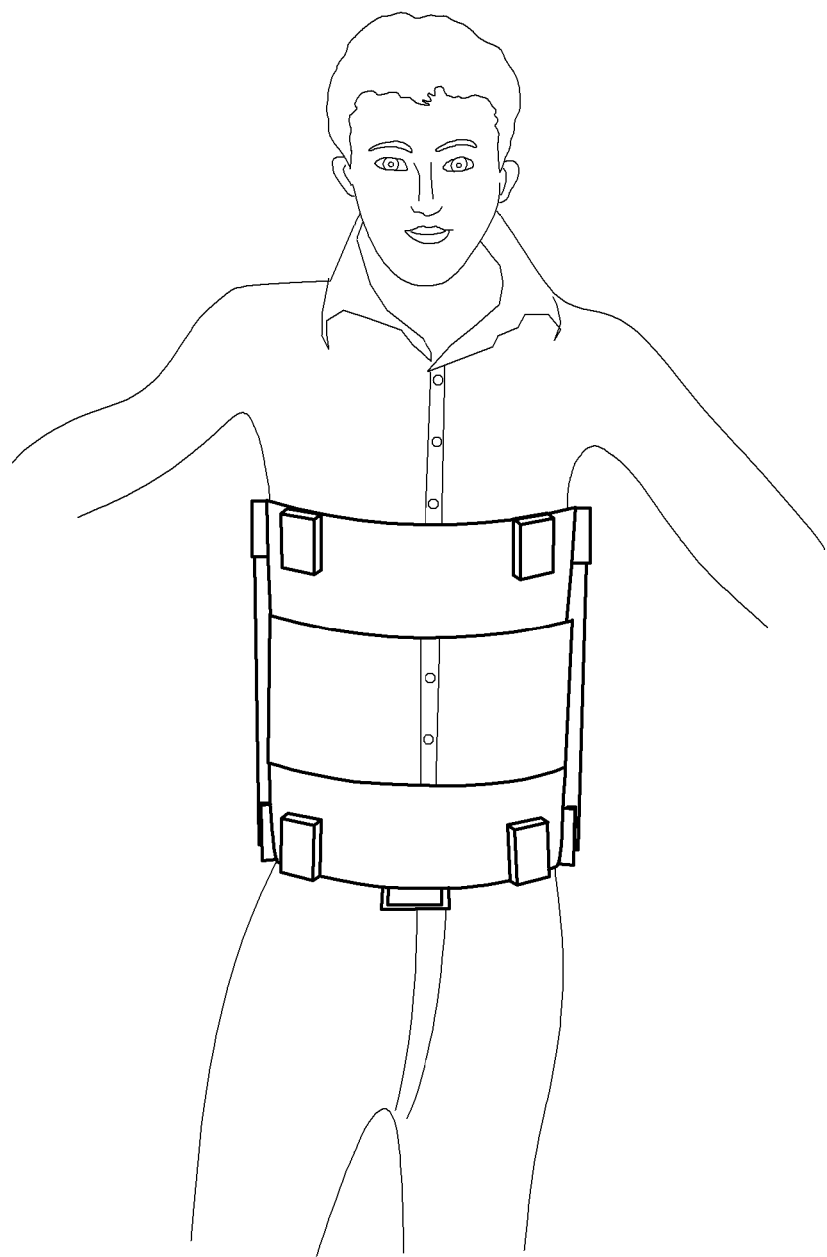
FIG. 1 shows an embodiment of the present invention being worn (outside clothing for clarity).

Turning to FIG. 1, an embodiment of the present invention is shown being worn. Each of the straps or belts is approximately five inches wide with sets of pockets on opposing edges. A splint can be seen extending vertically between the straps on each side of the body. The splints can be captured and held in place by the pockets. The pockets are optional; the splints can be permanently attached to the straps in some embodiments. Also, a plug or other device can be inserted into the holes at each end of the splint through the pocket and strap. The splint holes can be larger or smaller than the ¼" pictured in FIG. 7. FIG. 1 shows the device being worn outside the clothing for clarity. While this is possible, normally the device is worn under clothing so as to not be as visible.

Figure 2:
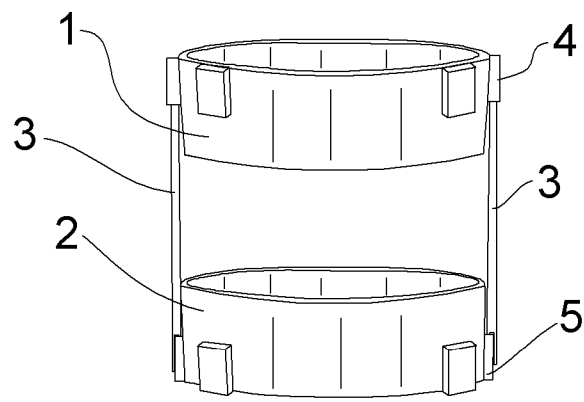
FIG. 2 shows the embodiment of FIG. 1 assembled, but not being worn.
Figure 3:
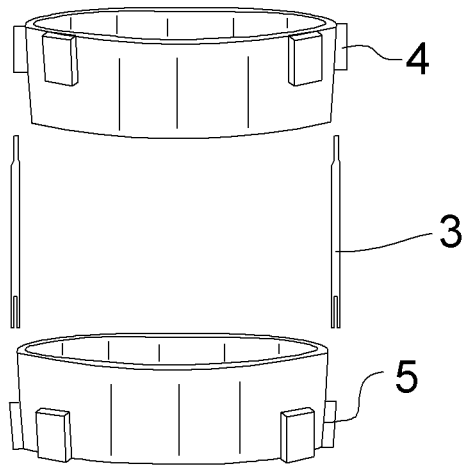
FIG. 3 shows an exploded view of the device of FIG. 2

FIG. 2 shows the device assembled, but not being worn, while FIG. 3 shows it exploded. The upper and lower straps 1, 2 are approximately five inches wide. Each strap can be approximately forty-five inches long with an overlapped region that uses hook-loop fasteners known in the trade as VELCRO™. Any other method may be used to secure the straps. The straps can thus be fitted to most wearers. Longer and shorter straps can be supplied for very large and very small wearers. While, the dimensions given are preferred, the straps can be made in any convenient sizes. The preferred material for the straps is neoprene; however, any flexible material may be used, including, but not limited to leather or other polymers.

FIGS. 2 and 3 also show a pair of splints 3 on the left and right sides of the device that are received and held by pockets 4, 5. The splints can be made from any rigid material with molded rigid plastic being preferred. Other materials can be metal or wood. Any material that is rigid as a flat splint can be used. The lower end of the splints can optionally be split or U-shaped to cup over a standard belt in the case the wearer prefers to wear only an upper strap. The splints are typically between eight to thirteen inches long with preferred sizes being approximately 9.00 inches, 10.75 inches and 12.00 inches. Any length of splint may be used. The splint extends from an upper strap under the shoulders to a lower strap on the belt line. The width of the splint can be between 1 inch and 3 inches with approximately 2 inches being preferred. The width of the splint is not critical as long as the splint fits snugly against the side of the body. The thickness of the splints can be between 0.15 inches to 0.25 inches with a preferred thickness being approximately 0.1875 inches. The thickness is not critical as long as the longest splint is thick enough to not bend outward in compression (column instability), but rather remain rigid.

It should be noted in FIGS. 1-3 that the splints 3 are located directly on the sides of the user's body. The are centered laterally. Centered laterally means that they are centered on right and left sides of the torso under the armpits. The optional additional pockets are only used so that different sized users can locate a splint directly on each side of their body, i.e. center it laterally. The device will not provide the required decompression if the splints are not on the sides of the body.

The pockets 4, 5 typically have slots that receive the splints. The pockets on the upper strap are typically on its upper edge, while the pockets on the lower strap are typically on its lower edge. The two straps can be identical with the lower strap simply flipped over when worn so that its pockets are on its lower edge. The slots should match the width and thickness of the splints so that they are held firmly in place by the straps 1, 2. As stated, the pockets are optional; the splints can be permanently attached to the straps by any known method.

Figure 4:
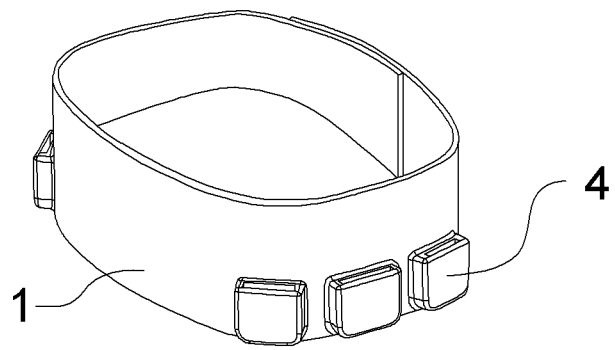
FIG. 4 shows an isometric view of one of the straps showing an arrangement of pockets.
Figure 5:
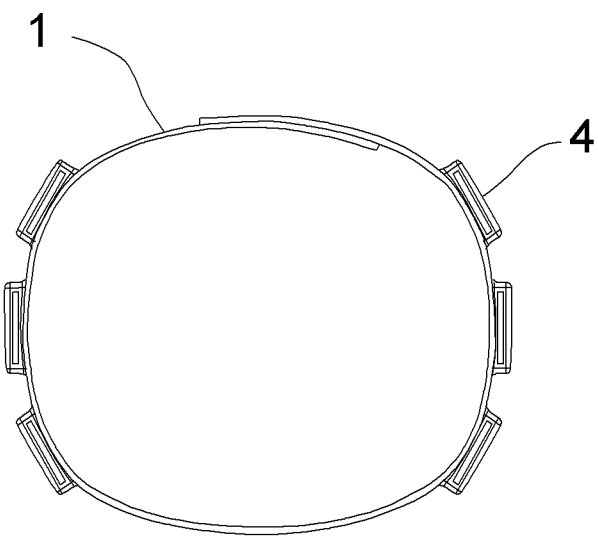
FIG. 5 shows a bottom-up view of the strap of FIG. 4.

FIGS. 4 and 5 show an embodiment of the strap 1 with three pockets 4 on the left and right sides. The center pocket is used for most users. Again, the extra, optional pockets are only used to assure that the splints are aligned with the left and right side of the user's body for different sized users. While three pockets are shown on each side, any number of pockets including only one pocket (or no pockets) on each side is within the scope of the present invention. The pockets 4 are securely attached to the strap 1. As stated, the preferred material for the strap 1 is neoprene, and the preferred material for the splint 3 is hard plastic.

Figure 6:
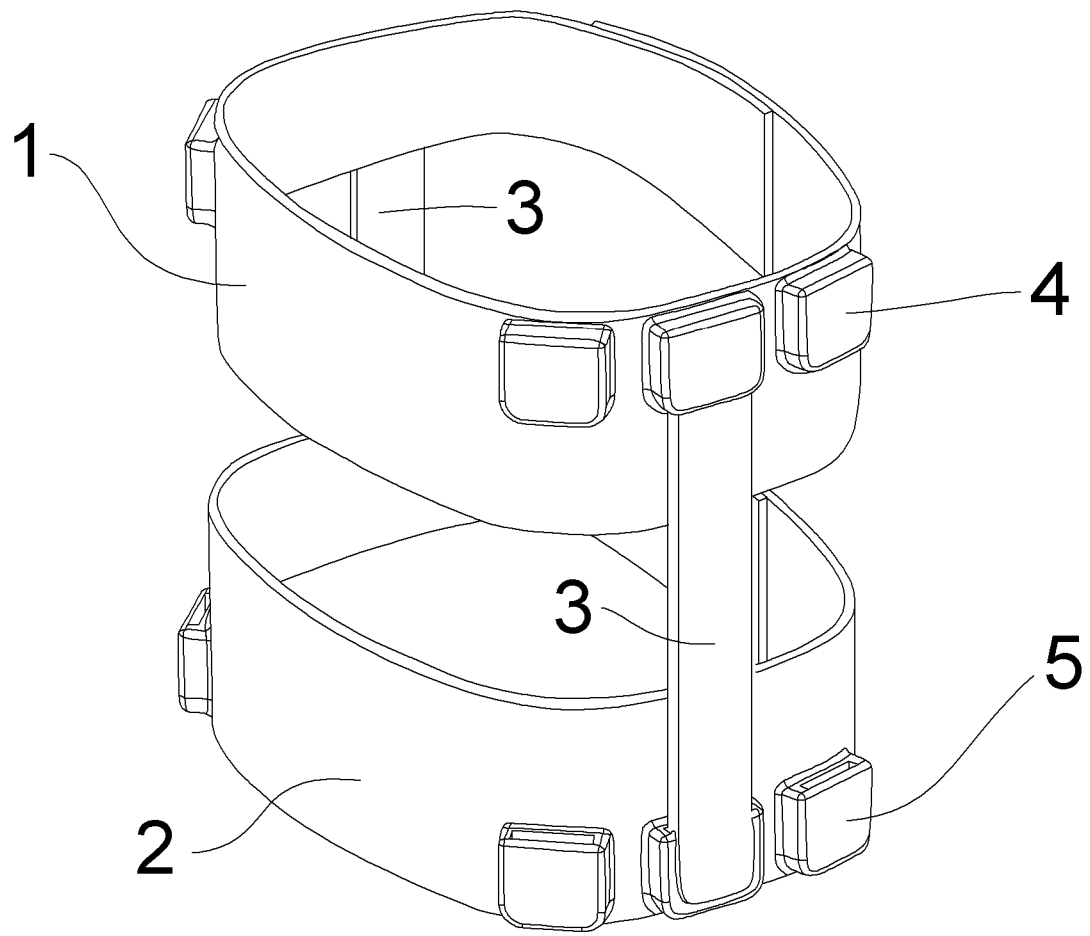
FIG. 6 shows a isometric view of an assembled version of the embodiment of FIGS. 4-5.

FIG. 6 shows the straps and splints of FIGS. 4-5 assembled. It should be noted that the top pockets 4 face downward, and the bottom pockets 5 face upward to receive and hold the splints. This alignment of the pockets occurs using identical straps for top and bottom by simply flipping the strap over depending upon whether it is used in the top or bottom position.

Figure 7:
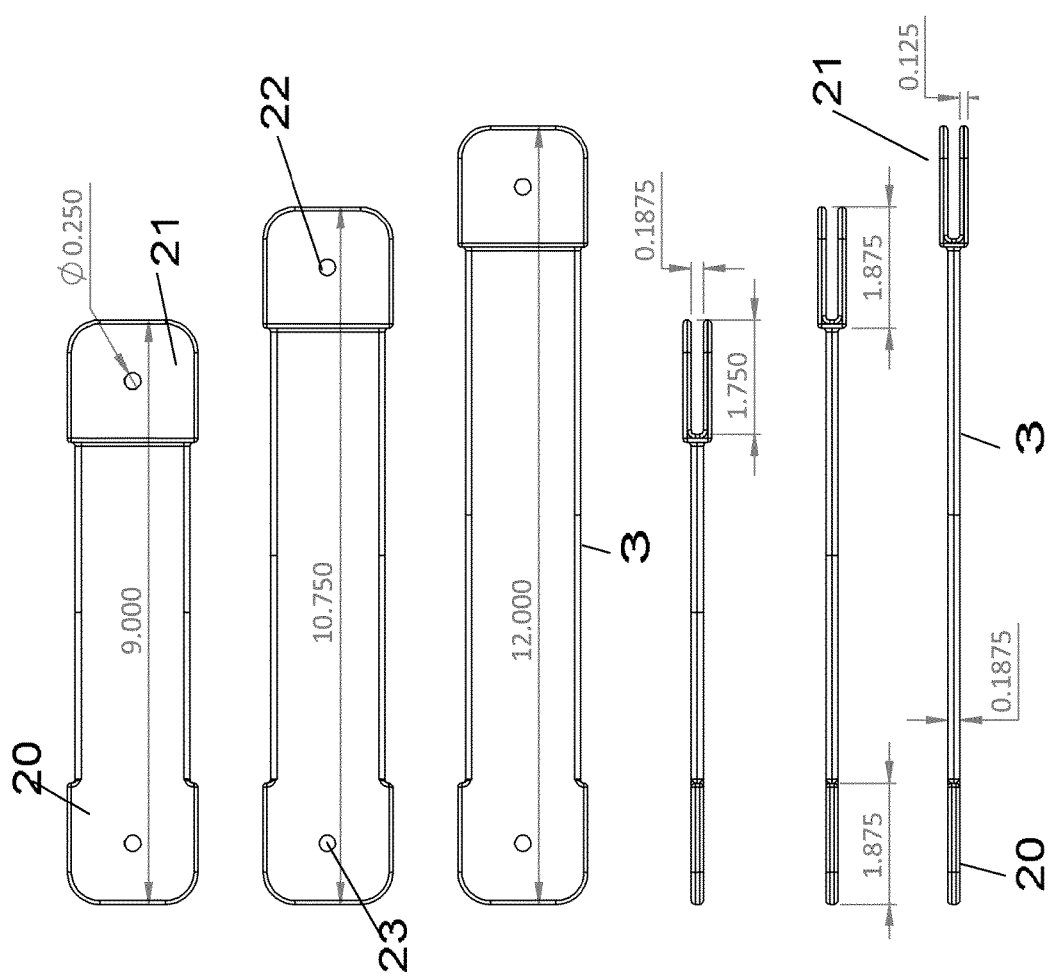
FIG. 7 shows top and side views of various length splints.

FIG. 7 shows top and side views of splints 3 of three preferred lengths 9.00 inches, 10.75 inches and 12.00 inches. Splints of these lengths can be supplied as stock items. Special splints of other sizes can also be made. Splints of any size are within the scope of the present invention. While other preferred dimensions are also shown in FIG. 7, all of the dimensions in FIG. 7 are for example only. The splints can be made with any other dimensions.

The splints 3 in FIG. 7 are shown with a flat end 20 and a forked or U-shaped end 21. The flat end 20 fits into the upper strap pocket 4, while the forked end 21 is the bottom end that either is received by the lower pocket 5 or forks around a standard belt worn around the hips. Splints can also be made with both ends flat or both ends forked.

The splints 3 of FIG. 7 are shown with small holes 23, 24 in their ends. These holes are optional, can be made any size, and can be used with removable plugs that secure the splints 3 to the pockets 4, 5. These, when used, allow the user to remove the belt and splints as a one-piece harness for convenience. However, plugs are typically not required to be used as the invention relies on the compressive forces between the straps 1, 2 to hold the splints 3 in the pockets 4, 5.

Figure 8:
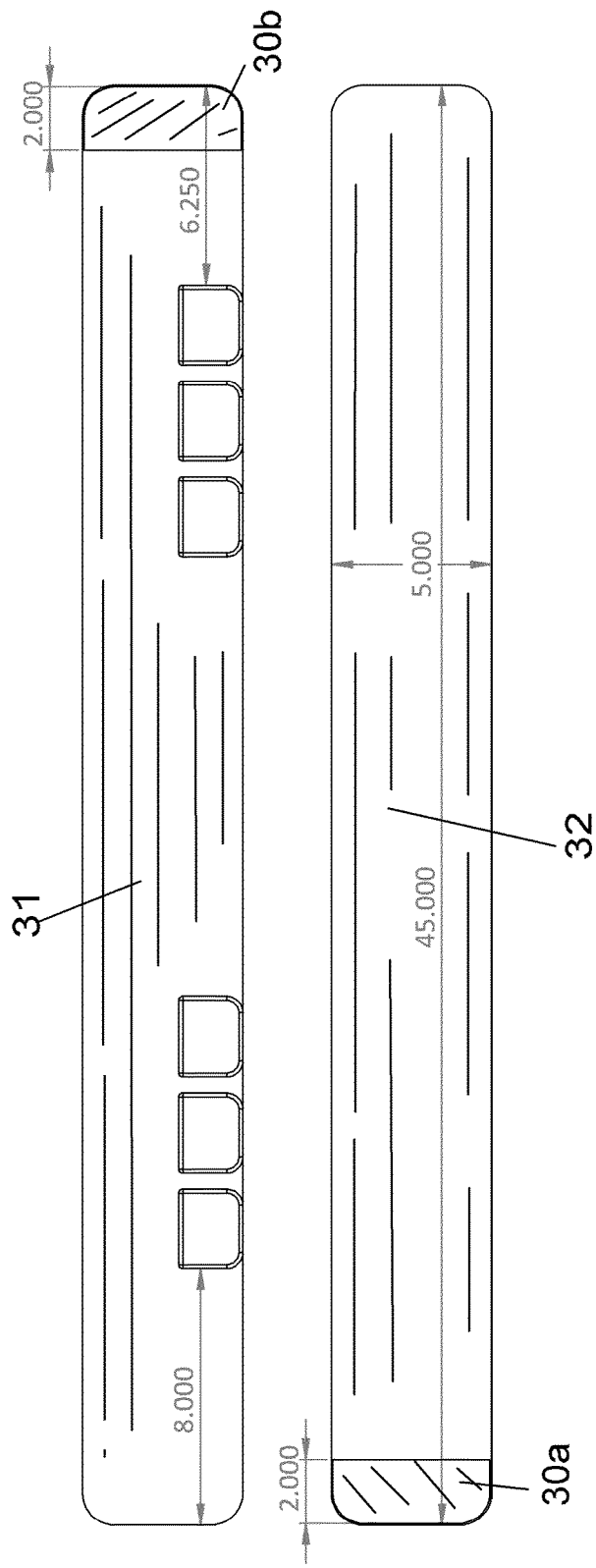
FIG. 8 shows a front and back view of a typical strap.

FIG. 8 shows a front and back view of a strap. FIG. 8 also shows example dimensions. Again, all of the dimensions in FIG. 8 are for example only. The straps can be made with any dimensions. The upper part of FIG. 8 shows the front of a representative strap; the lower part of FIG. 8 shows the back. Both the front and the back have a surface of loop material 31, 32. Hook material appears in strips 30a and 30b at the ends of the strap. There is hook material on both sides of the strap at different ends. This allows the strap to attach to the user's body at two different locations preventing slippage. While this is a particular embodiment of hook/loop material, any other arrangement of hook/loop material or any other method of holding the strap securely in place is within the scope of the present invention.

Figure 9:
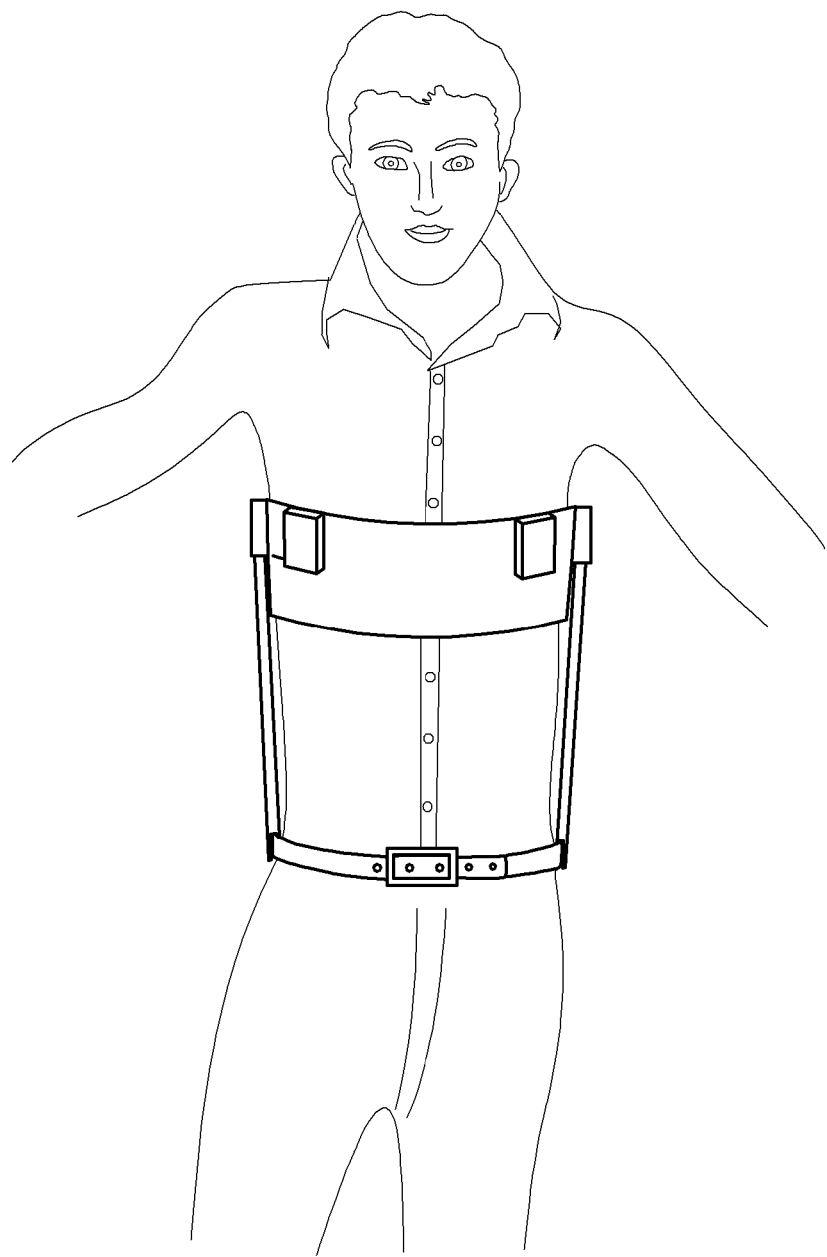
FIG. 9 shows an alternate embodiment of the invention worn with only one strap and a standard belt.

FIG. 9 shows an embodiment of the present invention being worn with only one strap using a standard belt for the lower strap. This embodiment may be preferred by users who do not wish to have to wear two straps. Again, the device is shown worn outside the user's clothing. Typically however, the device will be worn under clothing to make is less visible.

The present invention relates to a device that decompresses the lower spine of a wearer while standing or seated relieving pain from lower back problems and providing a better environment for long-term healing. In addition to Spinal Stenosis, the present invention is useful for general Spondylosis conditions such as, degenerative disc disease, herniated disks, sciatica, muscle spasms and other causes of lower back pain.

Several descriptions and illustrations have been presented to aid in understanding the present invention. One with skill in the art will realize that numerous changes and variations may be made without departing from the spirit of the invention. Each of these changes and variations is within the scope of the present invention.

I claim:

1. A method of relieving lower back pain using only a wearer's body weight comprising:
   providing a first flexible strap encircling a wearer's upper torso;
   providing a second flexible strap encircling the wearer's belt-line, or allowing the wearer to elect to use the wearer's belt or pants waistline as a lower flexible strap;
   providing a first continuous rigid splint along a left side of the wearer's body from the first flexible strap to the second flexible strap or to the wearer's belt or to the pants waistline;
   providing a second continuous rigid splint along a right side of the wearer's body from the first flexible strap to the second flexible strap or to the wearer's belt or to the wearer's pants waistline;
   wherein, the first and second continuous rigid splints have either split lower ends or U-shaped lower ends or flat lower ends constructed to allow use of the wearer's belt or pants waistline as a second flexible strap giving the wearer three options to anchor the bottom of the first and second rigid splints: (1) to use the wearer's pants belt, or (2) to use wearer's pants waist band, or (3) to use the second flexible strap;
   whereby the first and second rigid splints being to be coupled between the first and second flexible straps, or the first flexible strap and the wearer's belt or the first flexible strap and the wearer's pants waistband, respectively cooperating to transfer weight of a wearer's upper body, shoulders and head directly to the wearer's hips without mechanical coupling to the wearer's shoulders, said weight pressing downward on the first and second continuous rigid splints relieving lower back pressure by creating an upward reactive force on the wearer's lower spine thus stretching the wearer's lower spine upward relieving pressure on the wearer's lower vertebrae relieving lower back pain.

2. The method of claim 1 wherein lower ends of the first and second continuous rigid splints are received in and secured in pockets attached to the second flexible strap allowing the splints to move without pulling out of the pockets.

3. The method of claim 2 wherein the continuous rigid splints are secured in the pockets with hook and loop straps.

4. The method of claim 1 wherein upper ends of the first and second continuous rigid splints are received in first and second pockets respectively attached to the first flexible strap, the upper ends of the first and second continuous rigid splints being secured on one side of each splint to an inside of the first and second pocket respectively allowing the splints to rock forward, backward or sideways without pulling out of the pockets.

5. The method of claim 4 wherein the continuous rigid splints are secured in the pockets with hook and loop straps.

6. The method of claim 1 wherein the splints can be removed and the splints and straps rolled up as one piece when not in use.

7. The method of claim 1,
   further comprising allowing the wearer to use options (1), (2) and (3) simultaneously.

8. The method of claim 1 wherein the first and second flexible straps and the first and second continuous rigid splints are worn under the wearer's clothing.

9. A method of relieving lower back pain using only a wearer's body weight comprising:
   encircling a patient's upper torso with a first flexible strap;
   encircling the patient's belt-line with a second flexible strap, or allowing the wearer to use the wearer's belt or to use the wearer's waistband as a lower flexible strap
   placing a first continuous, rigid splint along a left side of the patient's body from the first flexible strap to the second flexible strap, or to the wearer's belt or to the wearer's waistline;
   placing a second continuous, rigid splint along a right side of the patient's body from the first flexible strap to the second flexible strap
   wherein, the first and second vertical splints, each having upper and lower ends, are removably attached at upper ends to the first flexible strap and removably attached at lower ends to the wearer's belt, the lower ends of the splints being U-shaped or split or flat to cup over a wearer's belt
   and wherein, the first flexible strap is constructed to grip the wearer's upper torso below the shoulders to not compress the wearers breasts or shoulder areas;
   whereby, the first and second rigid splints being optionally coupled between the first and second flexible straps, or the first flexible strap and the wearer's belt, or the first flexible strap and the wearer's pants waistband respectively cooperating to transfer weight of a wearer's upper body, shoulders and head directly to the wearer's hips without mechanical coupling to the wearer's shoulders, said weight pressing downward on the first and second continuous rigid splints relieving lower back pressure by creating an upward reactive force on the wearer's lower spine thus stretching the wearer's lower spine upward relieving pressure on the wearer's lower vertebrae relieving lower back pain.

10. The method of claim 9 wherein lower ends of the first and second continuous rigid splints are received in and secured in pockets attached to the second flexible strap, when the second flexible strap is provided, allowing the splints to move without pulling out of the pockets.

11. The method of claim 10 wherein the continuous rigid splints are secured in the pockets hook and loop straps.

12. The method of claim 9 wherein upper ends of the first and second continuous rigid splints are received in first and second pockets respectively attached to the first flexible strap, the upper ends of the first and second continuous rigid splints being secured on one side of each splint to an inside of the first and second pocket respectively allowing the splints to rock forward, backward or sideways without pulling out of the pockets.

13. The method of claim 12 wherein the continuous rigid splints are secured in the pockets with hook and loop straps.

14. The method of claim 9 wherein the splints can be removed and the splints and straps rolled up as one piece when not in use.

15. The method of claim 9, wherein lower ends of the first and second continuous rigid splints are attached to the wearer's belt using a U-shaped end on each splint.

16. The method of claim 9 wherein the first and second flexible straps and the first and second continuous rigid splints are worn under the wearer's clothing.

17. A method of relieving lower back pain of a wearer comprising:
providing a flexible strap configured to encircle the wearer's upper torso;
providing at least two vertical splints, each having upper and lower ends, the two vertical splints attached at upper ends to the flexible strap and attached at lower ends to the wearer's belt, the lower ends of the splints being U-shaped or split to cup over a wearer's belt or waist band; giving the wearer three options to anchor the bottom of the splint: (1) to use his or her own regular and typical pants belt, (2) to use the top rim of the wearer's pants waist band without any belt, or (3) to use a provided neoprene belt; wherein, the vertical splints are coupled between the flexible strap and the wearer's belt respectively, cooperating to transfer weight of a wearer's upper body, shoulders and head directly to the wearer's hips without mechanical coupling to the wearer's shoulders, said weight pressing downward on the first and second rigid splints relieving lower back pressure by creating an upward reactive force on the wearer's lower spine thus stretching the wearer's lower spine upward relieving pressure on the wearer's lower vertebrae relieving lower back pain;
wherein, the flexible strap is constructed to grip the wearer's upper torso below the shoulders to not compress the wearers breasts or shoulder areas.

18. The method of claim 17 wherein the flexible strap and splints are worn under the wearer's clothing.

* * * * *